(12) United States Patent
Takahashi

(10) Patent No.: US 7,070,560 B2
(45) Date of Patent: Jul. 4, 2006

(54) ILLUMINATION CONTROL SYSTEM AND METHOD FOR ENDOSCOPES

(75) Inventor: Tomoya Takahashi, Akiruno (JP)

(73) Assignee: Olympus Corporation, Tokyo (JP)

( * ) Notice: Subject to any disclaimer, the term of this patent is extended or adjusted under 35 U.S.C. 154(b) by 337 days.

(21) Appl. No.: 10/728,011

(22) Filed: Dec. 4, 2003

(65) Prior Publication Data

US 2004/0124791 A1 Jul. 1, 2004

Related U.S. Application Data

(63) Continuation of application No. PCT/JP02/11093, filed on Oct. 25, 2002.

(30) Foreign Application Priority Data

Oct. 26, 2001 (JP) .............................. 2001-329566

(51) Int. Cl.
*A61B 1/06* (2006.01)
(52) U.S. Cl. ................... 600/178; 600/180; 600/181; 362/574
(58) Field of Classification Search ............... 600/178, 600/180, 181, 109; 348/68–70; 362/572, 362/574

See application file for complete search history.

(56) References Cited

U.S. PATENT DOCUMENTS

| 4,509,508 | A | * | 4/1985 | Tsukaya | ............... | 600/118 |
| 5,220,912 | A | * | 6/1993 | Nakasima et al. | ............... | 600/109 |
| 6,320,331 | B1 | * | 11/2001 | Iida et al. | ............... | 315/293 |
| 6,464,633 | B1 | * | 10/2002 | Hosoda et al. | ............... | 600/178 |
| 6,724,418 | B1 | * | 4/2004 | Takahashi | ............... | 348/65 |

FOREIGN PATENT DOCUMENTS

| JP | 60-232523 | 11/1985 |
| JP | 61-177418 | 8/1986 |
| JP | 2000-75219 | 3/2000 |
| JP | 2000-171725 | 6/2000 |
| JP | 2000-201892 | 7/2000 |
| JP | 2001-204684 | 7/2001 |

* cited by examiner

*Primary Examiner*—John P. Leubecker
(74) *Attorney, Agent, or Firm*—Scully, Scott, Murphy & Presser, P.C.

(57) ABSTRACT

A light source device enables manual and automatic light regulation performed on illumination light that is irradiated to an object. A set value of a light regulation level for light emanating from a light source which is determined for use of an endoscope 11 is stored in a memory. When the driving power supply of the endoscope 11 is turned on again in order to reuse the endoscope, the stored and previously determined set value of the light regulation level is compared with a threshold value. When the previously determined set value of the light regulation level is equal to or larger than the threshold value, a diaphragm 26 is adjusted so that the light regulation level is set to a predetermined value. When the previously determined set value of the light regulation level is equal to or smaller than the threshold value, the diaphragm 26 is adjusted so that the light regulation level will be set to the previous determined set value.

16 Claims, 5 Drawing Sheets

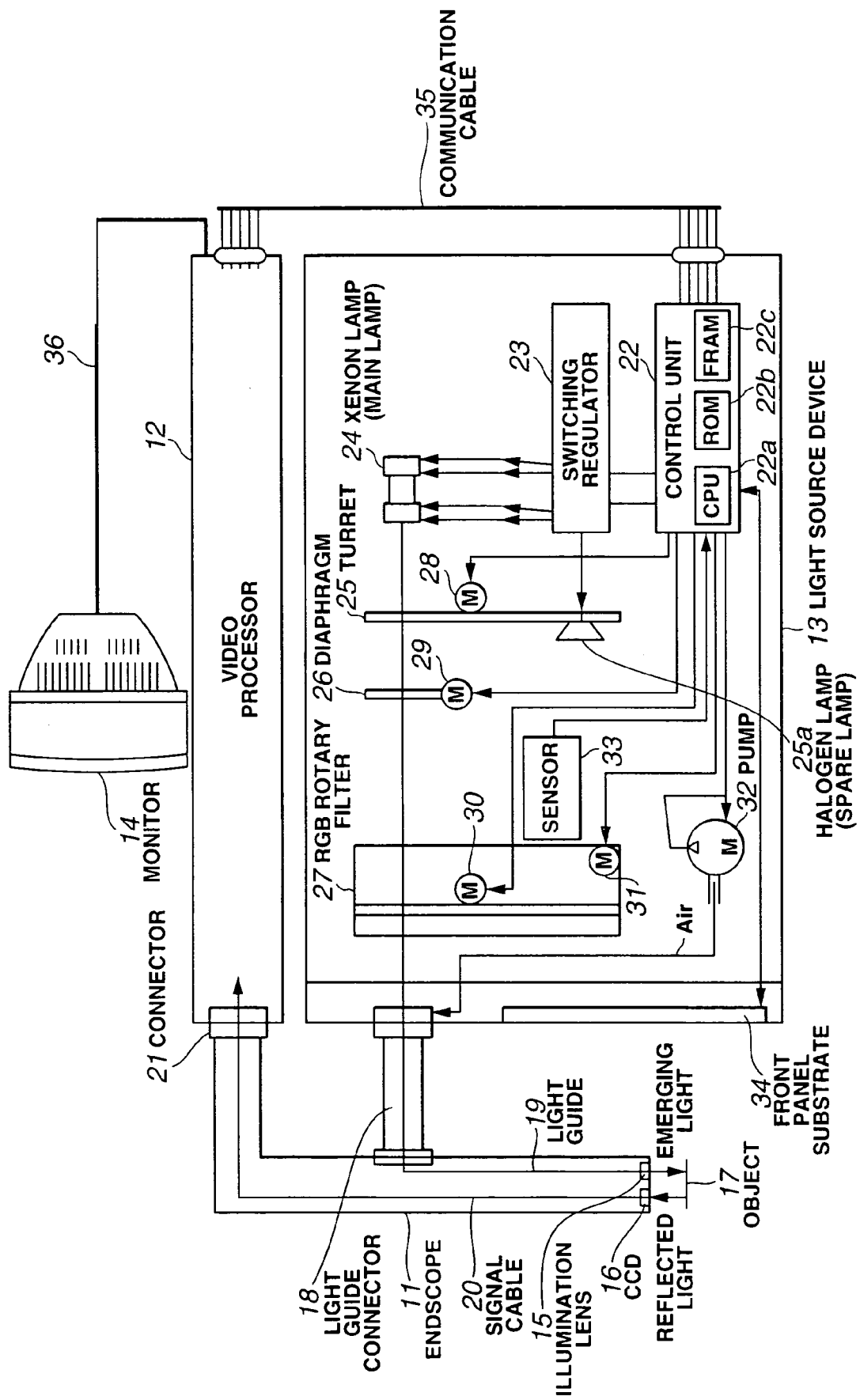

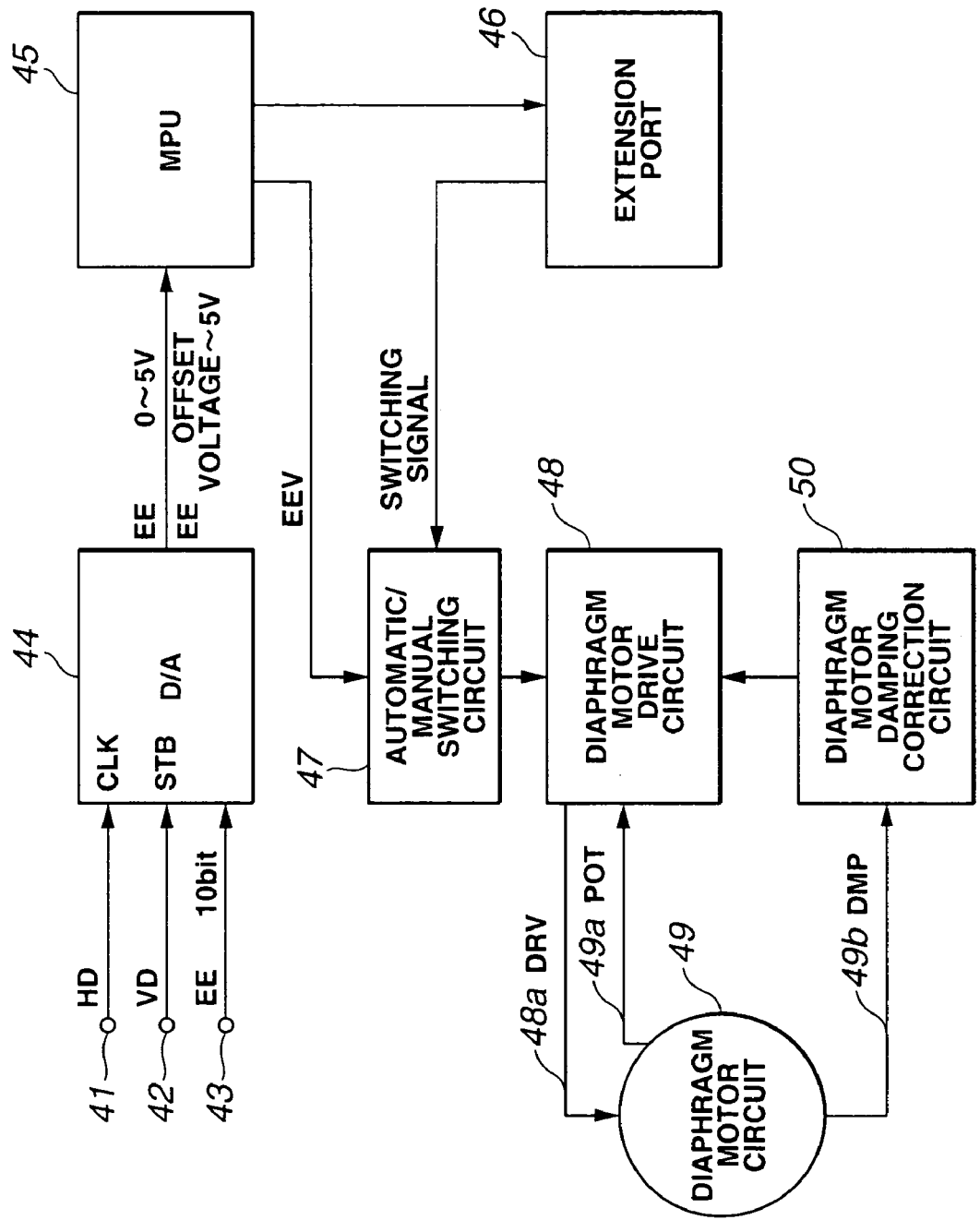

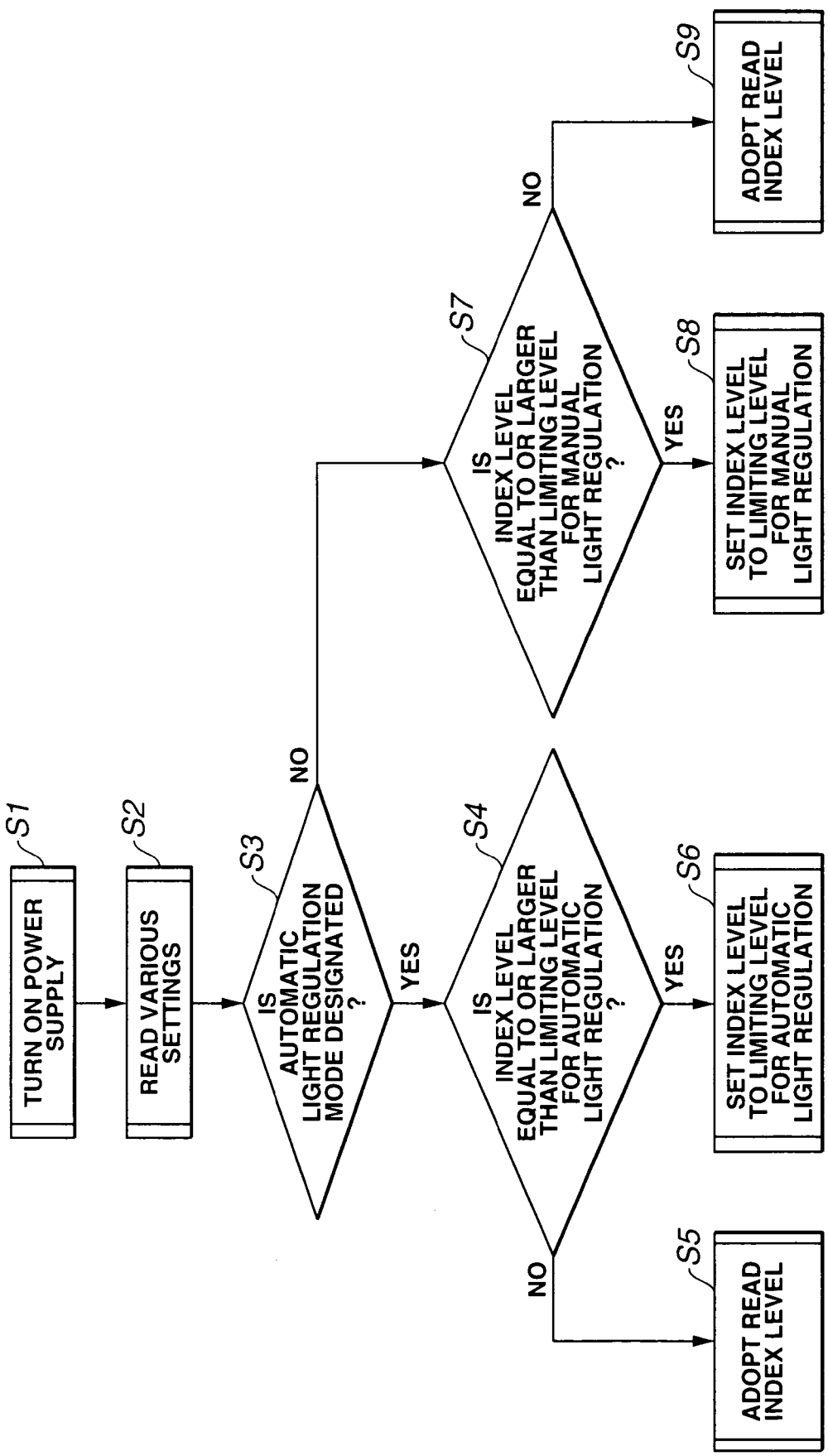

PRESENT INVENTING

ILLUMINATION CONTROL SYSTEM AND METHOD FOR ENDOSCOPES

CROSS REFERENCE TO RELATED APPLICATION

This application is a continuation application of PCT/JP02/11093 filed on Oct. 25, 2002 the disclosure of which is incorporated herein by its reference.

TECHNICAL FIELD

The present invention relates to an-illumination control system and method for endoscopes having a light source device that has a light regulation facility.

BACKGROUND ART

In the past, endoscope systems have been widely employed in diagnosis or observation of a body cavity or a thin lumen. An endoscope has an insertion unit that is inserted into the body cavity or thin lumen, and an operating unit for use in inserting the insertion unit in line with the internal shape of the body cavity or thin lumen. A light guide over which illumination light is guided, an image guide over which object light that is reflected light of the illumination light is guided, and the like are run through the operating unit and insertion unit alike. Moreover, the operating unit has an eyepiece member through which the object light guided over the image guide is viewed with naked eyes and a connector via which the light source device that supplies a predetermined amount of illumination light to the light guide is connected.

In recent years, electronic endoscope systems have been used in practice. The electronic endoscope system has a solid-state imaging device incorporated in the distal portion of the insertion unit or has a TV camera mounted on an eyepiece member of the operating unit. The solid-state imaging device or TV camera picks up object light that is reflected light of illumination light irradiated from the light guide, and produces an electronic image signal. After the electronic image signal is processed, an image is displayed on a monitor according to the resultant image signal.

When the endoscope system is used for diagnosis or observation, an amount of illumination light to be irradiated to a region to be diagnosed or observed, the wavelength thereof, and other operational conditions can be determined according to the region to be diagnosed or observed.

It takes much time to determine the operational conditions. In particular, it takes very much time to determine such operational conditions as a wavelength of illumination light and an amount thereof optimally to the region to be diagnosed or observed. Therefore, various operational conditions including the wavelength of illumination light and a magnitude of light regulation, which have been determined in order to perform diagnosis or observation using an endoscope system, are stored in a memory. When the endoscope system is used next, the previously determined operational conditions are read from the memory. Under the read operational conditions, the endoscope system is initialized so that diagnosis or observation can be performed. The initial operational conditions are modified optimally to a respective region to be diagnosed or observed. Endoscopic diagnosis or observation is then performed under the resultant operational conditions.

Consequently, the initial operational conditions under which the endoscope system performs diagnosis or observation can be determined quickly for a short period of time.

As mentioned above, the conventional endoscope system stores operational conditions, under which endoscopic diagnosis or observation has been performed, in a memory. When the endoscope system is reused for diagnosis or observation, the previous operational conditions are read from the memory and used to determine the initial operational conditions under which diagnosis or observation is performed next.

However, for example, assume that previous endoscopic diagnosis or observation is performed with a maximum amount of illumination light. After the diagnosis or observation is completed, when the driving power supply of an endoscope system is turned off, the operational conditions including an operational condition determined as the maximum amount of illumination light are stored in the memory.

After endoscopic diagnosis or observation is completed, when an endoscope is removed and put away, if the driving power supply is turned off by mistake with the maximum amount of illumination light adopted, the maximum amount of illumination light is stored in the memory.

Assuming that the endoscope system in which the previous operational conditions include the operational condition determined as the maximum amount of illumination light is used to diagnose or observe another region to be diagnosed or observed, when the driving power supply is turned on, the previous operational conditions are read from the memory. Consequently, the endoscope system is driven under the operational conditions including the operation condition determined as the maximum amount of illumination light.

Assume that a paramedic prepares the endoscope system, in which the maximum amount of illumination light has been adopted for the previous diagnosis or observation, for diagnosis or observation. After the driving power supply of the endoscope system is turned on, the endoscope system is left intact for some time until an operator actually starts endoscopic diagnosis or observation. Thus, a long time may elapse until actual diagnosis or observation starts.

In this case, the endoscope system is left intact with the maximum amount of illumination light adopted. The maximum amount of illumination light may heat, for example, a light guide connector that joins the light source device and endoscope system, an illumination lens located in front of the light guide at the distal end of the insertion unit of the endoscope system, or the insertion unit through which the light guide lies.

This poses a problem in that the heating deteriorates the light guide connector of the endoscope system, the illumination lens at the distal end of the insertion unit, or the insertion unit, or wastes driving power.

The electronic endoscope system has an automatic light regulation facility. Owing to the automatic light regulation facility, the luminance of an object image is calculated based on an object video signal produced by the solid-state imaging device, and an amount of illumination light to be supplied from the light source device is automatically controlled according to the calculated luminance. The automatic light regulation facility samples a luminance component from the object video signal produced by the solid-state imaging device. Based on the luminance component, the automatic light regulation facility performs light regulation by adjusting a diaphragm or a reduction filter located on the path of illumination light, controlling a lighting current that flows through a light source lamp, or the like.

In the electronic endoscope system, a communication cable linking a video processor that drives the solid-state imaging device so as to produce the object video signal, and the light source device that supplies illumination light to the endoscope system may be disconnected or incorrectly plugged in. Moreover, the communication facilities incorporated in the video processor and light source device may malfunction or fail. In this case, a luminance component is not transmitted from the video processor to the light source device. Consequently, the light source device determines that the object is the darkest. Consequently, driving is controlled in order to increase the amount of illumination light.

Accordingly, the amount of illumination light increases. Object light to be seen with naked eyes or electronically picked up is too bright to be used for diagnosis or observation. Moreover, the object light may cause heating.

The present invention attempts to break through the foregoing situation. An object of the present invention is to provide an illumination control system for endoscopes that even when the operational conditions determined for previous use include an operational condition determined as a maximum amount of illumination light, can adopt a suppressed amount of illumination light at the time of turning on a power supply. Thus, illumination light that is too bright to perform observation, heating, or wasting of driving power can be suppressed.

Another object of the present invention is to provide an illumination control system for endoscopes making it possible to automatically determine an optimal amount of illumination light for this time of endoscopic observation even when a previous operational condition is determined as a maximum amount of illumination light. Consequently, even if some time elapses from the instant preparations are made for endoscopic diagnosis or observation to the instant an operator actually performs endoscopic observation, heating will not occur. Thermal deterioration of an endoscope system can be alleviated.

DISCLOSURE OF INVENTION

An illumination control system for endoscopes in accordance with the present invention comprises:

a memory in which at least a set value of a light regulation level for light emanating from a light source is stored among various set values determined as various operational conditions for use of an endoscope system;

a reader for when the driving power supply of the endoscope system is turned on again in order to reuse the endoscope system, reading at least the set value of the light regulation level among the set values previously determined as the operational conditions and stored in the memory;

a comparator for comparing the previously determined set value of the light regulation level read by the reader with a predetermined threshold value; and a light level setting unit for: when the result of the comparison performed by the comparator demonstrates that the previously determined set value of the light regulation level is equal to or larger than the predetermined threshold value, setting the light regulation level for light emanating from the light source to a predetermined value; and when the previously determined set value of the light regulation level is equal to or smaller than the predetermined threshold value, setting the light regulation level for light emanating from the light source to the previously determined set value of the light regulation level.

Moreover, an illumination control method for endoscopes in accordance with the present invention comprises:

a storing step of storing in a memory at least a set value of a light regulation level for light emanating from a light source among various set values determined as various operational conditions for use of an endoscope system;

a reading step of when the driving power supply of the endoscope system is turned on again in order to reuse the endoscope system, reading at least the set value of the light regulation level among the set values previously determined as the operational conditions-and stored in the memory;

a comparing step of comparing the previously determined set value of the light regulation level read at the reading step with a predetermined threshold value; and a light level setting step of: when the result of the comparison performed at the comparing step demonstrates that the previously determined set value of the light regulation level is equal to or larger than the predetermined threshold value, setting the light regulation level for light emanating from the light source to a predetermined value; and when the previously determined set value of the light regulation level is equal to or smaller than the threshold value, setting the light regulation level for light emanating from the light source to the previously determined set value of the light regulation level.

Furthermore, an illumination light control method for endoscopes in accordance with the present invention comprises the steps of:

storing in a memory at least a set value of a light regulation level for light emanating from a light source among various set values determined as various operational conditions for use of an endoscope system;

when the driving power supply of the endoscope system is turned on again in order to reuse the endoscope system, reading at least the set value of the light regulation level among the set values previously determined as the operational conditions and stored in the memory;

comparing the read and previously determined set value of the light regulation level with a predetermined threshold value;

when the result of the comparison demonstrates that the previously determined set value of the light regulation level is equal to or larger than the predetermined threshold value, setting the light regulation level for light emanating from the light source to a predetermined value; and when the previously determined set value of the light regulation level is equal to or smaller than the threshold value, setting the light regulation level for light emanating from the light source to the previously determined set value of the light regulation level.

BRIEF DESCRIPTION OF THE DRAWINGS

FIG. 1 is a block diagram showing an endoscope system in which an embodiment of an illumination control system for endoscopes in accordance with the present invention is implemented.

FIG. 2 is a block diagram showing a light regulator included in the illumination light control system for endoscopes in accordance with the present invention.

FIG. 3 is a flowchart describing illumination light level setting by the illumination light control system for endoscopes in accordance with the present invention.

BEST MODE FOR CARRYING OUT THE INVENTION

Figure 4A:
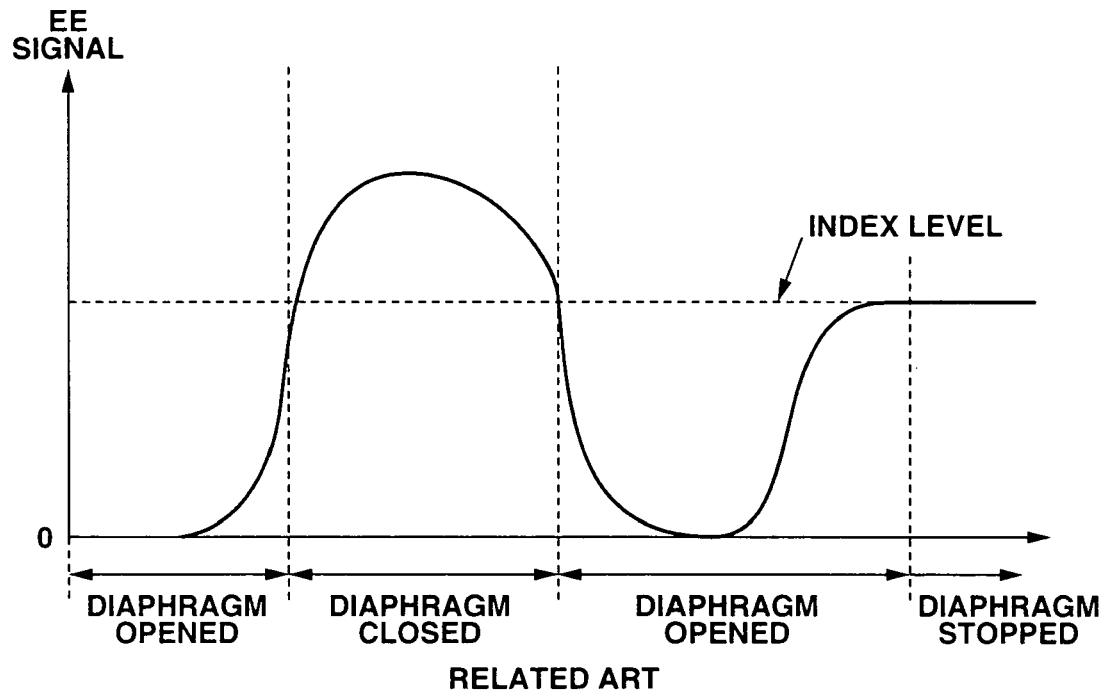
FIG. 4A and FIG. 4B are timing charts for explaining the relationship between a luminance signal by the illumination light control system and a diaphragm for endoscopes in accordance with the present invention.

Referring to the drawings, an embodiment of the present invention will be described below.

An endoscope system in which the embodiment is implemented comprises, as shown in FIG. 1, an endoscope (hereinafter a scope) 11, a video processor 12, a light source device 13, and a monitor 14.

An illumination lens 15 and a CCD 16 are incorporated in the distal portion of the endoscope 11. The distal end of a light guide 19 passed through a light guide connector 18 mounted on the proximal portion of the endoscope 11 is coupled to the illumination lens 15. A signal cable 20 passed through a connector 21 fixed to the proximal end of the endoscope 11 is coupled to the CCD 16.

Illumination light emitted from a light source 24 included in the light source device 13 that will be described later is guided over the light guide 19, and irradiated to an object 17 through the illumination lens 15. A driving signal which drives the CCD 16 and which is transmitted from the video processor 12, which will be described later, and an object video signal produced by the CCD 16 under object light reflected from the object 17 are transmitted over the signal cable 20.

The light guide 19 can be coupled to or decoupled from the light source device 13 owing to the light guide connector 18. The signal cable 20 can be coupled or decoupled from the video processor 12 owing to the connector 21.

The video processor 12 produces a driving signal which drives the CCD 16. Moreover, the video processor 12 produces a television video signal from the object video signal picked up by the CCD 16, and produces a video display signal according to which an object image picked up by the CCD 16 is displayed on the monitor 14.

The light source device 13 comprises a control unit 22, a switching regulator 23, a light source 24, a turret 25, a diaphragm 26, an RGB rotary filter 27, a pump 32, and a front panel substrate 34. The control unit 22 is connected to the video processor 12 over a communication cable 35. Based on a control signal sent from the control unit 22, the switching regulator 23 produces lighting power which lights the light source 24 that will be described later. The light source 24 is lit with the lighting power supplied from the switching regulator 23 and realized with a xenon lamp or the like that emits white light. The turret 25 is located on the path of the white light emitted from the light source 24. The turret 25 includes a normal filter that passes the white light and propagates a predetermined amount of light, a light reduction filter that reduces the white light to propagate a predetermined amount of light, an infrared filter that passes infrared light alone out of the white light, and an emergency lamp 25a such as a halogen lamp that is lit when the light source 24 cannot be lit. The diaphragm 26 is located on the path of the white light emitted from the light source 24, and controls an amount of light emitted from the turret 25. The RGB rotary filter 27 has three primary color filters of red, green, and blue filters that pass red, green, and blue light rays composed of the white light. Herein, the white light has emanated from the light source 24 and has been controlled to exhibit a predetermined light level by the diaphragm 26. The pump 32 causes water or air to flow through a water/air supply channel lying through the endoscope 11. The front panel substrate 34 has various buttons used to give operational instructions to the light source device 13, and also has various indicators that indicate the operating state of the light source device.

The control unit 22 comprises: a CPU 22a that is a microprocessor for controlling driving of the light source device 13; a ROM 22b in which various driving control sequences for the light source device 13 and data are held; and a ferroelectric memory (FRAM) 22c in which operational conditions under which various driving control sequences are followed with the driving power supply of the light source device 13 turned off are stored. The operational conditions under which the previous driving control sequence is followed and which are stored in the FRAM 22c are used as the operational conditions for the next driving control sequence.

The switching regulator 23 includes a stabilization circuit that produces lighting power which lights the light source 24 and that stabilizes the lighting power. Under the control of the control unit 22, the switching regulator 23 supplies the lighting power to the light source 24 or stops supplying it. Moreover, the switching regulator 23 has the ability to control a lighting current.

The turret 25 is shaped substantially like a disk and has the aforesaid normal filter, light reduction filter, infrared filter, the emergency lamp 25a and the like arranged on the perimeter thereof. The center shaft of the disk-shaped turret 25 is borne by the shaft of a motor 28. Under the driving control of the control unit 22, the motor 28 is driven to rotate. Consequently, a predetermined filter or the emergency lamp 25a is disposed on the path of the white light emanating from the light source 24.

A motor 29 is driven under the driving control of the control unit 22, whereby an opening of the diaphragm 26 is adjusted or controlled in order to pass a predetermined amount of illumination light that has emanated from the light source 24 and has passed through the turret 25.

The RGB rotary filter 27 has the red, green, and blue transmission filters arranged at predetermined intervals on the perimeter of the disk-like substrate thereof, though the color transmission filters are not shown. A portion of the RGB rotary filter 27 interposing between adjoining ones of the color transmission filters does not pass the illumination light emanating from the light source 24. Moreover, illumination light passing through the red, green, or blue transmission filter is propagated as red, green, or blue light. When a motor 30 is driven to rotate at a predetermined rotating speed and a predetermined rps under the control of the control unit 22, the RGB rotary filter 27 passes the red, green, and blue illumination light rays. The red, green, and blue illumination light rays are irradiated to the object 17 by way of the light guide 19 and illumination lens 15. The CCD 16 is exposed to object light that is reflected light of each of the red, green, and blue illumination light rays, whereby red, green, and blue object video signals are produced. That is to say, field—sequential imaging type video signals are produced.

Moreover, the RGB rotary filter 27 is removed from the path of illumination light emanating from the light source 24 by means of the motor 31 under the control of the control unit 22.

Furthermore, the RGB rotary filter 27 has a reflector, though not shown, which indicates a reference point, located at an initial start position relative to which the magnitude of the rotation of the color transmission filters is detected. A sensor 33 is included for detecting the reflector that indicates the reference point. The result of the detection performed by the sensor 33 is transmitted to the control unit 22.

The front panel substrate 34 has various operational buttons and operational indicators, for example, LEDs. The operational indicators include a display means that notifies a user of occurrence of an abnormality or a failure in the light source device 13. The abnormality notifying means is, for example, a facility for flickering a red LED or sounding a sounding element for the purpose of notifying a user of an abnormality.

When an operational button on the front panel substrate is manipulated, information concerning the operational button is transmitted to the control unit 22. In the control unit 22, the CPU 22a reads a control sequence associated with the operational button and relevant data from the ROM 22b. Based on the read control sequence and data, the CPU 22a controls driving of the switching regulator 23, the motors 28 to 31, and the pump 32.

In the endoscope system having the foregoing components, when a lighting button on the front panel substrate 34, which is used to light the light source 24, is manipulated, the CPU 22a in the control unit 22 reads a lighting control sequence, according which lighting the light source 24 is controlled, from the ROM 22b. According to the developed lighting control sequence, driving the light source 24, turret 25, diaphragm 26, and RGB rotary filter 27 are controlled.

To be more specific, the switching regulator 23 is driven so that the light source 24 is driven to be lit. Illumination light emanating from the light source 24 passes through any of the filters included in the turret 25 which is selected under the control of the control unit 22. The amount of illumination light is regulated by the diaphragm 26 whose aperture size is determined under the control of the control unit 22. The illumination light then falls on the RGB rotary filter 27. The RGB rotary filter 27 is driven to rotate at a predetermined rps under the driving control of the control unit 22. Red, green, and blue light rays produced by the red, green, and blue transmission filters are propagated to the light guide 19 through the light guide connector 18 at regular intervals. The red, green, and blue light rays propagated to the light guide 19 are irradiated to the object 17 through the illumination lens 15. The red, green, and blue light rays reflected from the object 17 are sequentially converged on the CCD 16, whereby red, green, and blue video signals are produced through photoelectric conversion.

On the other hand, the control unit 22 controls driving of the video processor 12 over the communication cable 35, and sequentially inputs the red, green, and blue video signals produced by the CCD 16 into the video processor 12. The timing of inputting the red, green, and blue video signals from the CCD 16 into the video processor 12 is controlled using a detection signal sent from the sensor 33 that has detected the reflector on the RGB rotary filter 27. Namely, the inputting is controlled to be synchronous with the rotation of the RGB rotary filter 27.

The red, green, and blue video signals produced by the CCD 16 and inputted into the video processor 12 are synthesized to produce a television video signal and a display signal which drives the monitor 14 in order to display an object image.

Furthermore, the video processor 12 samples luminance information from the red, green, and blue video signals, and transfers the luminance information to the control unit 22.

Based on the luminance information sent from the video processor 12, the control unit 22 drives the motor 29 to adjust the aperture of the diaphragm 26 so that object light may be optimized. Thus, an amount of light emanating from the light source 24 and falling on the RGB rotary filter 27 is automatically controlled.

As mentioned above, driving the diaphragm 26 is controlled based on luminance information sent from the video processor 12. Thus, light regulation is automatically performed. Otherwise, manual light level regulation buttons on the front panel substrate 34, which are not shown, may be used to regulate an amount of light. For example, when a light level increase button is manipulated, the control unit 22 drives the motor 29 to open the aperture of the diaphragm 26 responsively to the manipulation performed on the light level increase button. When a light level decrease button is manipulated, the control unit 22 drives the motor 29 to close the aperture of the diaphragm 26 responsively to the manipulation performed on the light level decrease button.

Referring to FIG. 3, routines performed when the foregoing endoscope system is reused will be described below. At step S1, the driving power supply of the light source device 13 is turned on. At step S2, various operational conditions determined for the previous use are read from the FRAM 22c included in the control unit 22. At step S3, it is determined whether among the read previously-determined various operational conditions, the operational condition for light regulation is determined as automatic light regulation.

When it is determined at step S3 that the previous operational condition for light regulation is determined as automatic light regulation, it is determined at step S4 whether a previously-determined index level indicating the aperture size of the diaphragm 26 for automatic light regulation is equal to or larger than a limiting level.

What is referred to as an index level is any of a plurality of levels associated with light levels, that is, amounts of transmitted light. The amount of light depends on the size of the aperture determined with the angle of aperture blades included in the diaphragm 26. For example, the number of index levels is five or ten, and the lowest level is associated with dark and the highest level is associated with bright.

Moreover, what is referred to as a limiting level is a light level of illumination light with which the light guide connector 18, light guide 19, and illumination lens 15 are heated, or in other words, an index level causing heating to start. Incidentally, the limiting level for automatic light regulation is determined based on a distance to an object and an amount of light.

When it is determined at step S4 that the previous index level is equal to or smaller than the limiting level for automatic light regulation (a light level not causing heating), a diaphragm motor drive circuit 48 is driven at step S5 in order to set the diaphragm 26 to the previous index level read at step S2.

When it is determined at step S4 that the previous index level is equal to or larger than the limiting level of an amount of light (a light level causing heating), the diaphragm motor drive circuit 48 is driven at step S6 in order to set the diaphragm 26 to the limiting level of an amount of light for automatic light regulation (a light level not causing heating).

When it is determined at step S3 that the previous light regulation is manual light regulation, it is determined at step S7 whether the previously determined index level indicating the aperture size of the diaphragm 26 is equal to or larger than a limiting level for manual light regulation. The limiting level for manual light regulation refers to a limit of an amount of light that should not be exceeded because otherwise heating occurs.

For manual light regulation, an amount of light is determined based on the size of the light transmission aperture of the diaphragm 26 dependent on the angle of the aperture blades. Therefore, the limiting level for manual light regulation depends on the angle of the aperture blades permitting transmission of a limiting amount of illumination light that does not cause heating.

When it is determined at step S7 that the previous index level is equal to or larger than the limiting level for manual light regulation (a light level not causing heating), the diaphragm motor drive circuit 48 is driven at step S8 in order to set the diaphragm 26 to the limiting level for manual light regulation (a light level not causing heating).

When it is determined at step S7 that the previous index level is equal to or smaller than the limiting level for manual light regulation (a light level not causing heating), the diaphragm motor drive circuit 48 is driven at step S9 in order to set the diaphragm 26 to the previous index level read at step S2.

In other words, when the previous amount of illumination light is equal to or larger than a heating limiting level, the diaphragm is set to an index level equal to or smaller than the heating limiting level. When the previous amount of illumination light is equal to or smaller than the heating limiting level, the diaphragm is set to the previous set value equal to or smaller than the heating limiting level. Thus, heating by illumination light occurring from the instant the endoscope system gets ready to the instant actual diagnosis or observation is started can be avoided, and deterioration of the endoscope system stemming from heating can be prevented.

The limiting level for automatic or manual light regulation is the heating limiting level indicating a limit of an amount of light that should not be exceeded because otherwise heating occurs. Any of index levels equal to or smaller than the heating limiting level may be set. For example, when the driving power supply is turned on, illumination light may not be transmitted at all. Otherwise, the diaphragm 26 may be set to an index level indicating an amount of illumination light with which an illuminating state can be barely discerned. Otherwise, an operator or a paramedic may determine a setting freely.

Assume that among the previously determined operational conditions, an operational condition may be determined in such a manner that a special filter, for example, the infrared filter of the turret 25 should be selected. In this case, when the driving power supply is turned on, the previously determined operational condition concerning the turret 25 may be canceled so that the normal filter can be selected without fail.

Furthermore, when it is determined at step S3 that a manual light regulation mode is designated, the light regulation mode may be switched to an automatic light regulation mode. Otherwise, when the driving power supply is turned off, the currently determined operational conditions may be cleared and reset to predetermined ones.

Next, a light regulator will be described in detail in conjunction with FIG. 2. Red, green, and blue video signals produced by the CCD 16 exposed to red, green, and blue light rays through photoelectric conversion are synthesized to produce a composite television video signal by means of the video processor 12, and also converted into a digital video signal. A luminance signal component of the digital video signal is converted into a digital luminance signal EE of 10 bits long having been impressed on a predetermined offset voltage. The digital luminance signal EE having been offset, a horizontal sync signal HD, and a vertical sync signal VD are transferred to a digital-to-analog converter (D/A converter) 44. This results in an analog luminance signal EE. The analog luminance signal EE ranges from the offset voltage to 5 V because the digital luminance signal has been impressed on the predetermined offset voltage as described above (When the digital luminance signal EE is not offset, a luminance signal EE provided by the D/A converter 44 ranges from 0 to 5 V). The analog luminance signal EE produced by the D/A converter 44 is transferred to the microprocessor (hereinafter an MPU) 45. The MPU 45 calculates a driving voltage EEV, which drives the diaphragm 26, from the analog luminance signal EE received from the D/A converter 44. The calculated driving voltage EEV is produced by the D/A converter 44 included in the MPU 45, and then transferred to the diaphragm motor drive circuit 48 via an automatic/manual switching circuit 47.

Automatic light regulation or manual light regulation is selected using a light level regulation switching button located on the control panel substrate 34. At this time, information on which of automatic light regulation and manual light regulation has been selected is transferred to the MPU 45. Based on the information, a switching signal to be transferred to the automatic/manual switching circuit 47 via an extension port 46 is produced.

The diaphragm motor drive circuit 48 produces a driving signal (DRV) 48a, which drives a motor unit 49 (a unit added to the motor 29 for the diaphragm 26 shown in FIG. 1), on the basis of the driving voltage EEV received from the MPU 45 via the automatic/manual switching circuit 47. With the driving signal (DRV) 48a, the diaphragm motor unit 49 drives the diaphragm 26 to a specific index level.

The diaphragm motor unit 49 includes a sensor that detects the angle of the aperture blades determining the aperture size of the diaphragm 26, and a sensor that detects a magnitude of motor damping in the diaphragm motor 29. The angle-of-aperture blades detecting sensor transmits an angle-of-aperture blades detection signal (POT) 49a to the diaphragm motor drive circuit 48. The motor damping sensor for the diaphragm motor 29 transmits a damping signal (DMP) 49b to a diaphragm motor damping correction circuit 50.

The diaphragm motor damping correction circuit 50 produces a damping correction signal for the diaphragm motor 29 on the basis of the damping signal (DMP) 49b, and transmits the damping correction signal to the diaphragm motor drive circuit 48. Based on the damping correction signal, the angle of the aperture blades of the diaphragm 26, that is, the aperture size of the diaphragm 26 is corrected.

Routines performed by the light regulator having the foregoing components will be described in conjunction with FIG. 4A and FIG. 4B. Conventionally, as shown in FIG. 4A, when the luminance signal EE has a low level, the motor drive circuit 48 is driven in a direction permitting the diaphragm 26 to open. When the luminance signal EE has a high level, the diaphragm motor drive circuit 48 is driven in a direction permitting the diaphragm 26 to close. At this time, the communication cable 35 linking the video processor 12 and light source device 13 may not be connected or may be disconnected. Otherwise, the luminance signal EE sent from the video processor 12 to the D/A converter 44 in the light source device 13 may have a zero level because of imperfect attachment of a connector or the like. In this case, the MPU 45 determines that an amount of light is insufficient, and drives the diaphragm motor drive circuit 48 in the direction permitting the diaphragm 26 to open. Eventually, the diaphragm 26 is fully opened in order to increase the amount of illumination light propagated from the illumination lens 15 incorporated in the endoscope 11.

Consequently, a maximum amount of illumination light caused by the diaphragm 26 that is fully opened falls on the light guide connector 18, illumination lens 15, and light guide 19 included in the endoscope 11, and heats them.

Figure 4B:
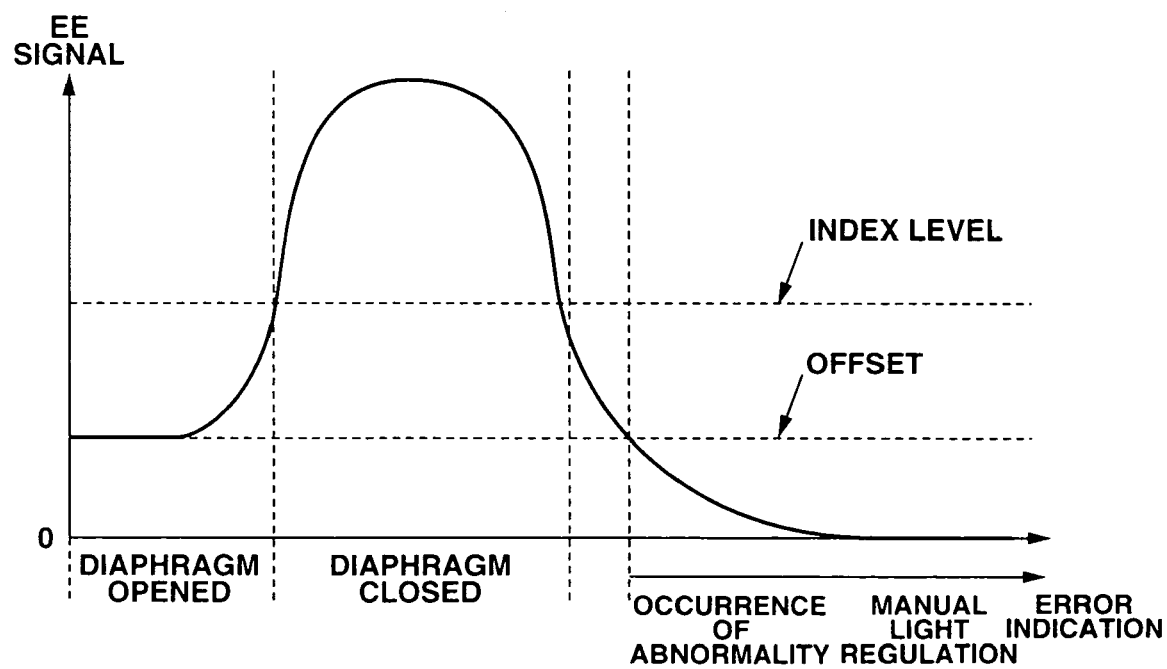

In the endoscope system in which the present invention is implemented, as shown in FIG. 4B, the luminance signal EE is impressed on an offset voltage. When the luminance signal EE is equal to or smaller than the offset voltage, it is determined that the luminance signal EE produced by the video processor 12 is not transmitted to the light source device 13 over the communication cable 35, that is, an abnormality has occurred. Consequently, for example, the red LED on the front panel substrate 34 serving as an emergency notifying means is flickered or the sounding element is driven to generate an abnormality notifying sound. At the same time, the diaphragm 26 is driven to pass an amount of light not causing heating.

Routines performed by the MPU 45 included in the light regulator will be described in conjunction with FIG. 5A and FIG. 5B. FIG. 5A describes the routines of the MPU included in a conventional light regulator. At step S11, a luminance signal EE is received from the video processor. At step S12, it is determined whether the received luminance signal EE indicates an index level corresponding to a predetermined standard amount of light (hereinafter a predetermined index level).

The predetermined index level can be determined by an operator, and varied depending on a region to be diagnosed or observed among the plurality of index levels associated with light levels, that is, amounts of illumination light.

When it is determined at step S12 that the luminance signal EE indicates an index level smaller than the predetermined index level, the diaphragm motor drive circuit 48 is driven in order to increase an amount of light passing through the diaphragm 26 at step S14.

When it is determined at step S12 that the luminance signal EE indicates an index level larger than the predetermined index level, the diaphragm motor drive circuit 48 is driven in order to decrease an amount of light passing through the diaphragm 26 at step S13.

When the diaphragm motor drive circuit 48 is driven at step S13 or S14, the diaphragm motor unit 49 is driven at step S15 in order to change the amount of light passing through the diaphragm 26. Control is then returned to step S11.

The luminance signal EE may not be transferred from the video processor 12 to the light regulator included in the light source device 13 for some reason. In this case, the luminance signal EE indicates an index level smaller than the predetermined index level. The MPU 45 therefore controls driving in a direction permitting the diaphragm 26 to increase an amount of light to be passed. This increase in the amount of light brings about heating and eventually deteriorates the endoscope 11.

Figure 5B:
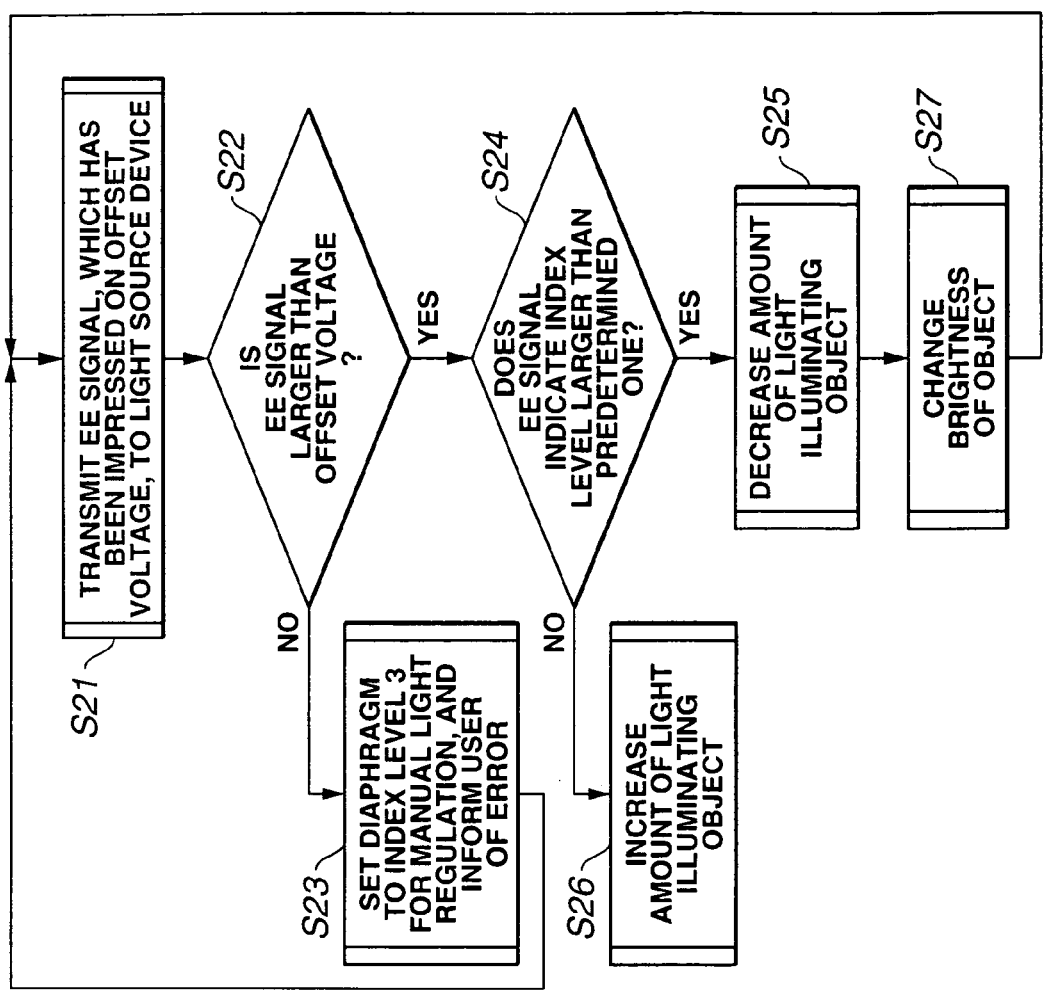
FIG. 5A and FIG. 5B are flowcharts describing illumination light level limitation by the illumination control system for endoscopes in accordance with the present invention.
Figure 5A:
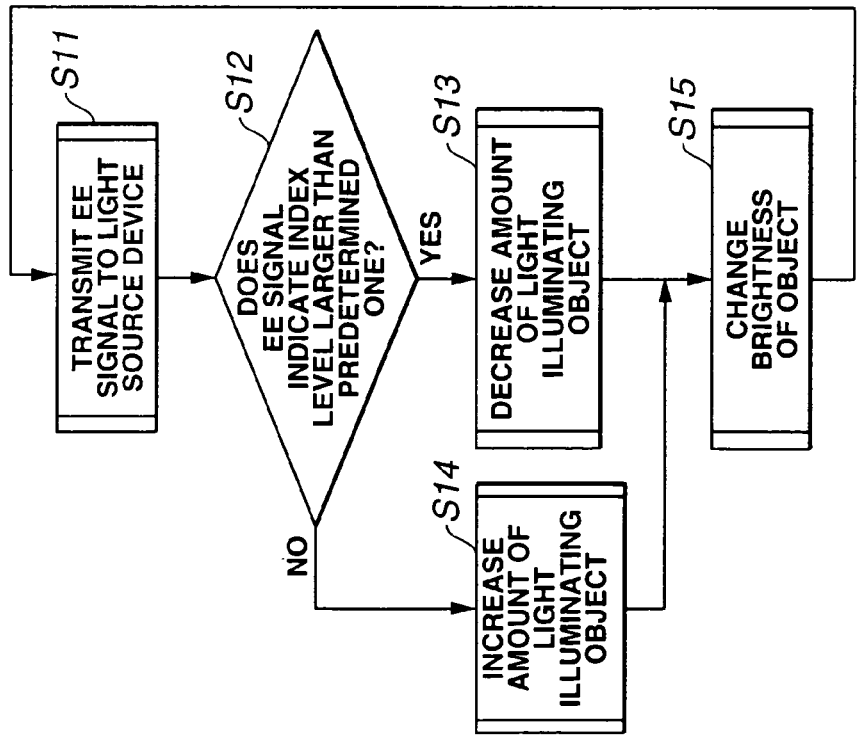

In contrast, as described in FIG. 5B, the light regulator included in the light source device 12 in the endoscope system in which the present invention is implemented inputs a luminance signal EE, which has been impressed on an offset voltage by the video processor 12, into the MPU 45 at step S21. At step S22, it is determined whether the inputted offset luminance signal EE is equal to or larger than the offset voltage. When it is determined that the offset luminance signal EE is equal to or smaller than the offset voltage, the diaphragm motor drive circuit 48 is driven in order to set the diaphragm 26 to a predetermined index level designated by an operator at step S23. The predetermined index level is, for example, index level 3 that is an intermediate index level among five index levels. Moreover, the LED on the front panel substrate 34 is flickered or the abnormality notifying sound is generated, whereby an operator or a paramedic is notified that the luminance signal is abnormal. Control is then returned to step S21.

When it is determined at step S22 that the offset luminance signal EE inputted from the video processor 12 is equal to or larger than the offset voltage, step S24 and succeeding steps are carried out.

Step S24 and succeeding steps are identical to step S12 and succeeding steps in FIG. 5A. Step S24 corresponds to step S12, step S25 corresponds to step S13, step S26 corresponds to step S14, and step S27 corresponds to step S15. The description of the steps is omitted.

As fully described so far, the endoscope system in which the present invention is implemented copes with a case where a maximum amount of illumination light is designated for endoscopic diagnosis or observation or designated by mistake when an endoscope system is put away after completion of the endoscopic diagnosis or observation. In this case, the maximum amount of illumination light is stored in a memory as one of the previously determined operational conditions. When the endoscope system in which the previously determined operational conditions are stored in the memory is used for another diagnosis or observation, diagnosis or observation is performed under the stored previously determined operational conditions. At this time, among the previously determined operational conditions, the operational condition determined as the maximum amount of illumination light may be changed to a predetermined amount of illumination light with which the light guide connector, light guide, and illumination lens incorporated in the endoscope may not be heated. Consequently, deterioration of the endoscope stemming from heating can be prevented.

Moreover, the communication cable linking the video processor and light source device may be disconnected, the joint connector fixed to the communication cable may be connected incorrectly or imperfectly, or the signal transfer facilities incorporated in the video processor and light source device may malfunction. In this case, luminance information is not transmitted from the video processor to the light source device. Consequently, the light regulating facility included in the light source device determines that an amount of illumination light is insufficient and works to increase the amount of light. In the endoscope system in which the present invention is implemented, luminance information produced by the video processor is impressed on a predetermined offset voltage. When the luminance information represents a voltage equal to or smaller than the offset voltage, the light regulating facility included in the light source device sets the amount of illumination light to a predetermined amount of illumination light, and notifies an operator of the fact. Consequently, an abnormal state in which the amount of illumination light is abnormal can be avoided, and the operator can be notified of occurrence of an abnormality.

Conventional endoscope systems have to preserve or maintain various kinds of data concerning the operational conditions for endoscopic diagnosis or observation, maintenance of the endoscope system such as disinfection or sterilization thereof, a repair service for the endoscope system, and implementation of endoscopic diagnosis or observation.

The various kinds of enormous data concerning the endoscope system is stored and preserved in a battery-driven RAM or a nonvolatile memory. However, as far as the battery-driven RAM is concerned, when a battery is managed unsuccessfully, the data stored in the RAM may be lost. This necessitates a data backup.

As for the nonvolatile memory, it takes much time to write or read data. Moreover, the number of times of writing is limited. Therefore, the same limitation must be imposed on a data backup.

In order to preserve and manage enormous data for a long period of time, a ferroelectric memory (FRAM) is adopted as a memory means for preservation or management of the various kinds of data. It takes little time to write or read data in or from the FRAM. Besides, a backup battery is unnecessary. Furthermore, the number of times of writing is not limited. The FRAM has improved the reliability of data held for a long period of time.

As described in relation to the embodiment of the present invention, the aperture size of the diaphragm 26 is adjusted in order to regulate an amount of illumination light. Alternatively, the reduction filter included in the turret 25 may be disposed on the light path, or a lighting current supplied from the switching regulator 23 to the light source 24 may be regulated in order to supply the predetermined amount of light.

The embodiment of the present invention has been described so far. The present invention is not limited to the embodiment but can be modified in various manners without a departure from the spirit of the present invention.

INDUSTRIAL APPLICABILITY

As described above, according to the present invention, even if one of operational conditions is determined for previous use as a maximum amount of illumination light, a suppressed amount of illumination light can be automatically set at the time of turning on the power supply this time. Consequently, irradiation of light that is too bright for observation, heating, and wasting of driving power can be suppressed. Even if some time elapses from the instant preparations are made for endoscopic diagnosis or observation to the instant an operator actually performs endoscopic observation, heating may not occur. Thermal deterioration of an endoscope system can be alleviated.

The invention claimed is:

1. An illumination control system for endoscopes comprising:
a memory in which at least a set value of a light regulation level for light emanating from a light source is stored among various set values determined as various operational conditions for use of an endoscope system;
a reader for, when a driving power supply of the endoscope system is turned on again in order to reuse the endoscope system, reading at least the set value of the light regulation level among the set values previously determined as the operational conditions and stored in the memory;
a comparator for comparing the previously determined set value of the light regulation level read by the reader with a predetermined threshold value; and
a light level setting unit for: when the result of the comparison performed by the comparator demonstrates that the previously determined set value of the light regulation level is equal to or larger than the predetermined threshold value, setting the light regulation level for light emanating from the light source to a predetermined value; and when the previously determined set value of the light regulation level is smaller than the predetermined threshold value, setting the light regulation level for light emanating from the light source to the previously determined set value of the light regulation level.

2. An illumination control system for endoscopes according to claim 1, further comprising a regulator for regulating the light regulation level for light emanating from the light source.

3. An illumination control system for endoscopes according to claim 2, wherein the regulator includes a first regulator enabling manual regulation of the light regulation level and a second regulator enabling automatic regulation of the light regulation level.

4. An illumination control system for endoscopes according to claim 3, wherein when the previously determined set value of an amount of light is a value determined by the second light level regulator, the comparator adopts a first predetermined value determined based on a distance to an object and an amount of light.

5. An illumination control system for endoscopes according to claim 3, wherein when the previously determined set value of an amount of light is a value determined by the first light level regulator, the comparator adopts a value determined based on the angle of aperture blades included in a diaphragm.

6. An illumination control system for endoscopes according to claim 3, wherein when the previously determined set value of an amount of light is a value determined by the first light level regulator, the comparator cancels manual light regulation that is previously determined and adopts a predetermined value of an automatic light regulation level.

7. An illumination control system for endoscopes according to claim 2, wherein the regulator for regulating the light regulation level for light emanating from the light source drives or controls a diaphragm located on the path of illumination light.

8. An illumination control system for endoscopes according to claim 2, wherein the regulator for regulating the light regulation level for light emanating from the light source disposes a light reduction filter on the path of illumination light so as to supply a predetermined amount of light.

9. An illumination control system for endoscopes according to claim 2, wherein the regulator for regulating the light regulation level for light emanating from the light source controls a lighting current which lights the light source of illumination light.

10. An illumination control system for endoscopes according to claim 1, wherein when the driving power supply of the endoscope system is turned on again, a normal filter that passes illumination light emanating from the light source is disposed on a light path irrespective of which of various optical filters included in a turret has been used previously.

11. An illumination control system for endoscopes according to claim 10, wherein the various optical filters include an infrared filter.

12. An illumination control system for endoscopes according to claim 1, wherein when the driving power supply of the endoscope system is turned off, the set values determined as various operational conditions for use of the endoscope system are cleared, and the operational conditions are set to predetermined values.

13. An illumination control system for endoscopes according to claim 1, wherein the threshold value is equal to or smaller than a heating limiting value, the threshold value being compared with the previously determined set value of the light regulation level by the comparator.

14. An illumination control method for endoscopes comprising:
a storing step of storing in a memory at least a set value of a light regulation level for light emanating from a light source among various set values determined as various operational conditions for use of an endoscope system;

a reading step of, when a driving power supply of the endoscope system is turned on again in order to reuse the endoscope system, reading at least the set value of the light regulation level among the set values previously determined as the operational conditions and stored in the memory;

a comparing step of comparing the previously determined set value of the light regulation level read at the reading step with a predetermined threshold value; and a light level setting step of: when the result of the comparison performed at the comparing step demonstrates that the previously determined set value of the light regulation level is equal to or larger than the predetermined threshold value, setting the light regulation level for light emanating from the light source to a predetermined value; and when the previously determined set value of the light regulation level is smaller than the threshold value, setting the light regulation level for light emanating from the light source to the previously determined set value of the light regulation level.

15. An illumination control method for endoscopes according to claim 14, further comprising a regulating step of regulating the light regulation level for light emanating from the light source, wherein:

the regulating step includes a first regulating step enabling manual regulation of the light regulation level and a second regulating step of enabling automatic regulation of the light regulation level.

16. An illumination control method for endoscopes comprising the steps of:

storing in a memory at least a set value of a light regulation level for light emanating from a light source among various set values determined as various operational conditions for use of an endoscope system;

when a driving power supply of the endoscope system is turned on again in order to reuse the endoscope system, reading at least the set value of the light regulation level among the set values previously determined as the operational conditions and stored in the memory;

comparing the previously determined set value of the light regulation level with a predetermined threshold value;

when the result of the comparison demonstrates that the previously determined set value of the light regulation level is equal to or larger than the predetermined threshold value, setting the light regulation level for light emanating from the light source to a predetermined value; and when the previously determined set value of the light regulation level is smaller than the threshold value, setting the light regulation level for light emanating from the light source to the previously determined set value of the light regulation level.

* * * * *